(12) United States Patent
Gliner et al.

(10) Patent No.: US 12,579,812 B2
(45) Date of Patent: Mar. 17, 2026

(54) VERIFICATION OF PHACOEMULSIFICATION TIP TYPE USING IMAGE PROCESSING

(71) Applicant: JOHNSON & JOHNSON SURGICAL VISION, INC., Irvine, CA (US)

(72) Inventors: Vadim Gliner, Haifa (IL); Eran Haas, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 66 days.

(21) Appl. No.: 18/526,608

(22) Filed: Dec. 1, 2023

(65) Prior Publication Data

US 2025/0182484 A1 Jun. 5, 2025

(51) Int. Cl.
| | |
|---|---|
| *A61M 3/02* | (2006.01) |
| *A61B 90/00* | (2016.01) |
| *A61B 90/20* | (2016.01) |
| *A61B 90/92* | (2016.01) |
| *A61F 9/007* | (2006.01) |
| *G06V 10/75* | (2022.01) |
| *G06V 20/50* | (2022.01) |
| *A61B 17/00* | (2006.01) |

(52) U.S. Cl.
CPC .............. G06V 20/50 (2022.01); A61B 90/20 (2016.02); A61B 90/361 (2016.02); A61B 90/92 (2016.02); A61F 9/00745 (2013.01); G06V 10/75 (2022.01); A61B 2017/00119 (2013.01); A61B 2017/00725 (2013.01); G06V 2201/034 (2022.01)

(58) Field of Classification Search
CPC .. G06V 20/50; G06V 10/75; G06V 2201/034; A61B 90/20; A61B 90/361; A61B 90/92; A61B 2017/00119; A61B 2017/00725; A61F 9/00745
See application file for complete search history.

(56) References Cited

U.S. PATENT DOCUMENTS

| | | | |
|---|---|---|---|
| 9,597,009 B2 | 3/2017 | Ren et al. | |
| 9,933,606 B2 | 4/2018 | Saur et al. | |
| 2018/0042772 A1* | 2/2018 | Mansour | A61F 9/00736 |
| 2018/0092774 A1* | 4/2018 | Mehta | G16H 50/50 |

(Continued)

FOREIGN PATENT DOCUMENTS

| | | |
|---|---|---|
| EP | 1667067 A1 | 6/2006 |
| EP | 3881793 A1 | 9/2021 |

(Continued)

*Primary Examiner* — Howard D Brown, Jr.

(57) ABSTRACT

A method for validating selection of a tip type for a tip of a handpiece of an ophthalmic instrument, the method includes storing a definition of multiple tip types and multiple respective visual properties of the tip types. An image of the tip is acquired by a camera during a medical procedure using the ophthalmic instrument. An actual visual property of the tip is identified in the acquired image. Based on the stored definition of the multiple tip types and the multiple respective visual properties, it is determined whether the actual visual property of the tip matches a specified tip type intended for the medical procedure. A responsive action is taken in case of a mismatch between the actual visual property and the specified visual property.

18 Claims, 2 Drawing Sheets

(56) References Cited

U.S. PATENT DOCUMENTS

| | | | |
|---|---|---|---|
| 2018/0168737 A1* | 6/2018 | Ren | A61B 90/36 |
| 2019/0000314 A1 | 1/2019 | Awdeh | |
| 2019/0000563 A1 | 1/2019 | Schneider et al. | |
| 2019/0099526 A1* | 4/2019 | Hajishah | A61F 9/00745 |
| 2019/0099547 A1* | 4/2019 | Mehta | A61M 3/0216 |
| 2022/0104884 A1 | 4/2022 | Leiderman et al. | |
| 2023/0255821 A1* | 8/2023 | Gliner | A61F 9/00736 |
| | | | 606/107 |
| 2024/0221152 A1* | 7/2024 | Kono | A61B 6/465 |

FOREIGN PATENT DOCUMENTS

| | | | |
|---|---|---|---|
| WO | 9959510 A1 | 11/1999 | |
| WO | 2023100124 A1 | 6/2023 | |

* cited by examiner

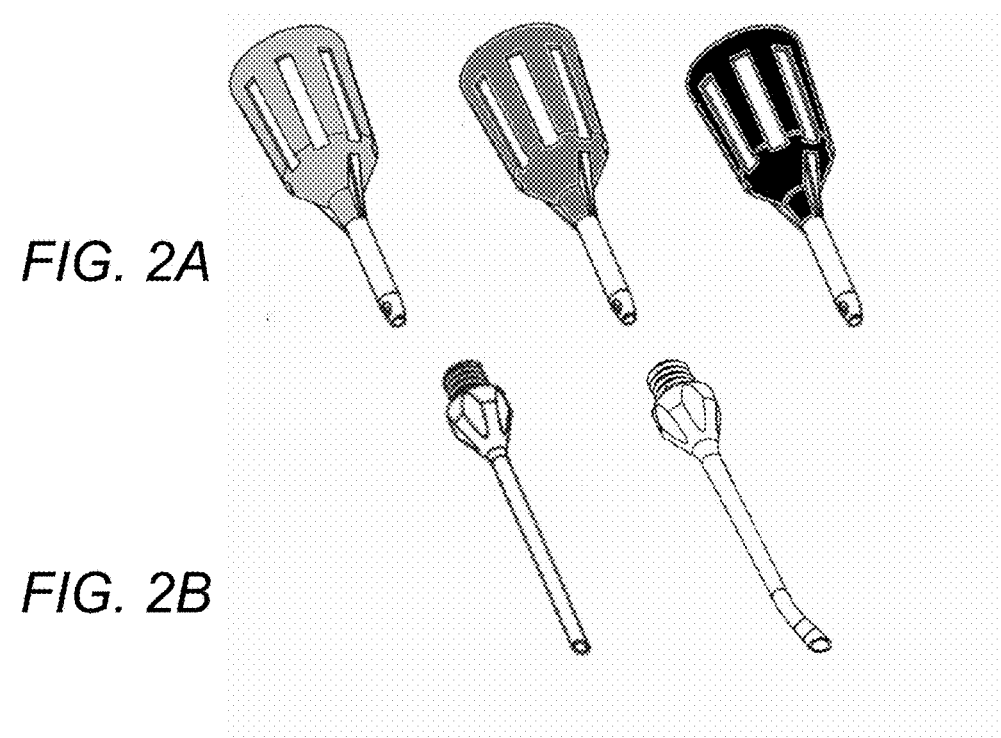
*FIG. 2A*
*FIG. 2B*
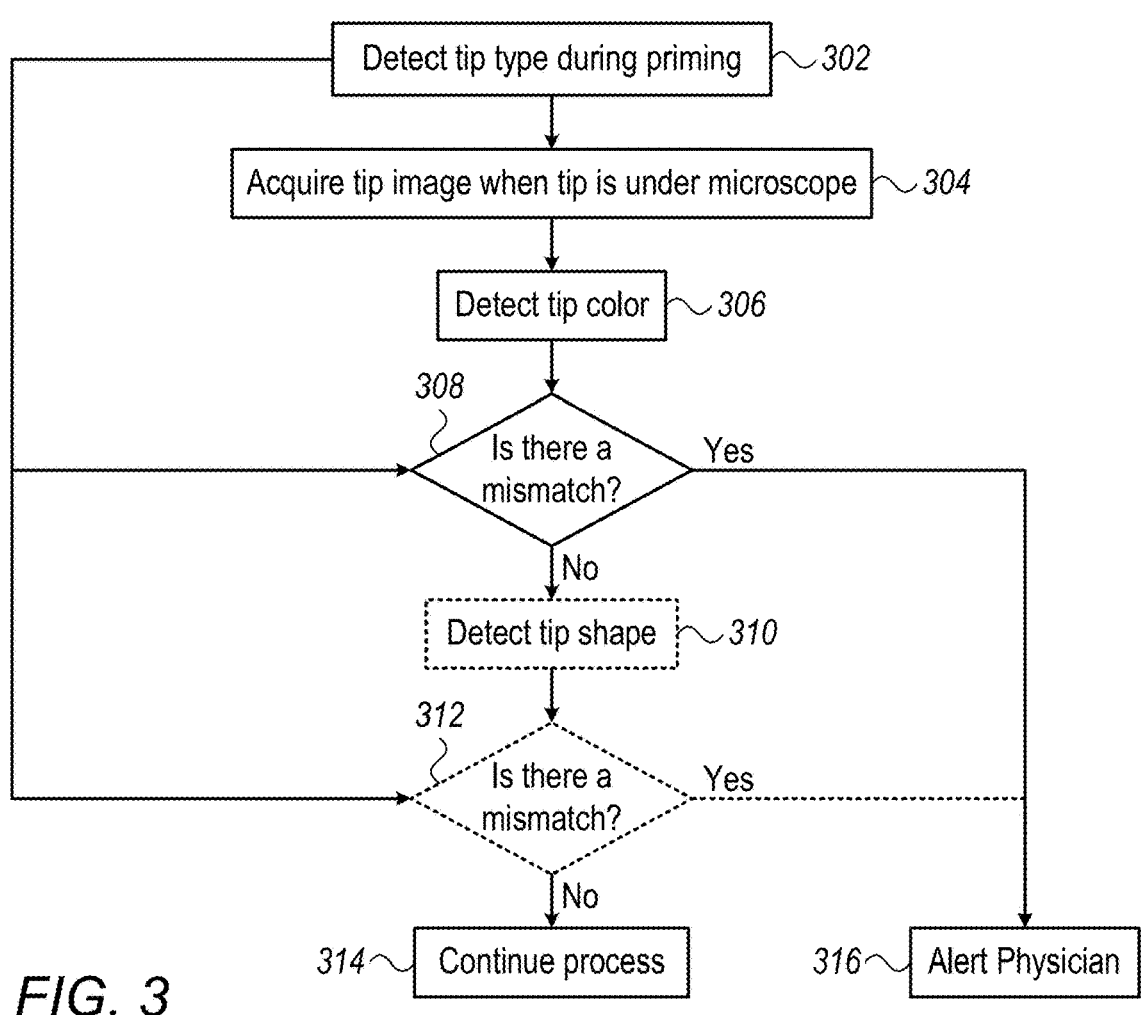
*FIG. 3*

VERIFICATION OF PHACOEMULSIFICATION TIP TYPE USING IMAGE PROCESSING

TECHNICAL FIELD

The present disclosure relates generally to natural lens removal device handpieces, and particularly to methods and systems for verifying the tip being used on a handpiece.

BACKGROUND OF THE DISCLOSURE

Ophthalmic surgical apparatuses, such as those used in phacoemulsification procedures, typically include operating controls for regulating settings or functions of the apparatus. Numerous types of apparatuses include as part of the apparatus, a hand-held medical implement or tool, such as a handpiece with a tip. Operation of the tool requires control of various operating settings or functions based on the type of tool used. Such apparatuses typically include a control module, power supply, an irrigation source, one or more aspiration pumps, as well as associated electronic hardware for operating a multifunction handheld surgical tool in order to sonically emulsify eye tissue, irrigate the eye with a saline solution, and aspirate the emulsified lens from the eye.

Different tip types are used in phacoemulsification procedures. Each tip type is different in both needle and sleeve diameter. The pressure offset and maximal flow that can be achieved depends on the tip type being used.

BRIEF DESCRIPTION OF THE DRAWINGS

The present disclosure will be more fully understood from the following detailed description of the examples thereof, taken together with the drawings in which:

FIGS. 2A and 2B are schematic diagrams of different possible sleeve colors (2A) and needle shapes (2B), of handpiece tips of the disclosed system in accordance with examples of the present disclosure; and FIG. 3 is a flow chart of a method for verifying tip type using image processing, in accordance with an example of the present disclosure.

DETAILED DESCRIPTION OF EXAMPLES

Overview

Figure 1:
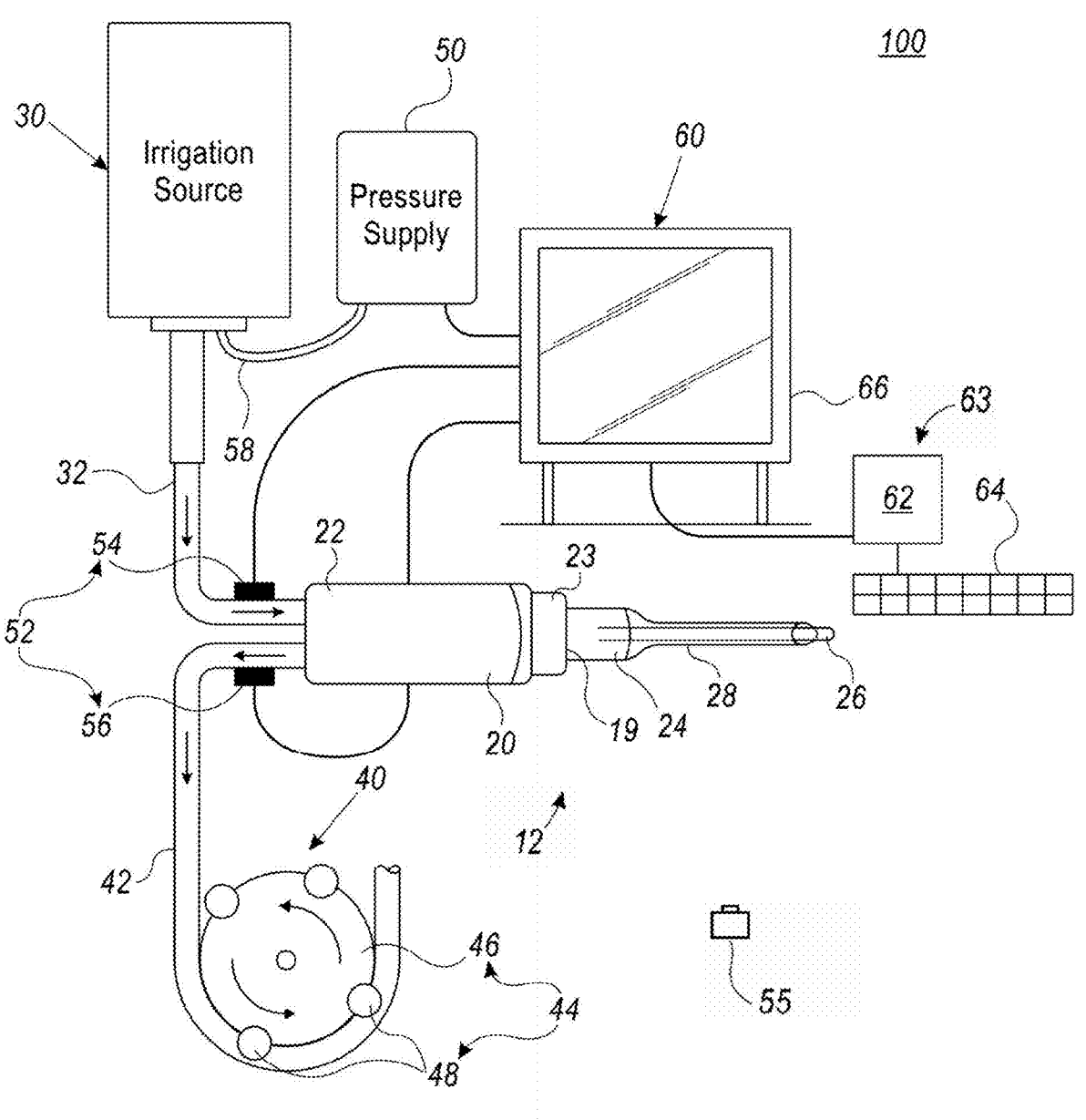
FIG. 1 is a schematic illustration of an ophthalmic surgical system, in accordance with an example of the present disclosure.

When performing ophthalmic surgical procedures, such as phacoemulsification or vitrectomy procedures, the physician may be required to identify or verify the tip type being used. As used herein, tip type or tip means the irrigation sleeve, the phacoemulsification needle, or the combination of an irrigation sleeve and phacoemulsification needle. The irrigation sleeve at least partially surrounds the phacoemulsification needle. Identifying or verifying the tip type attached to the handpiece ensures the tip type is compatible with the system, the correct system settings are being used for the tip type, and/or the system settings are adjusted to suit the tip type.

In another example, identification of the sleeve only, the needle only, or the combination of the sleeve and needle are envisioned. The color and/or shape of the sleeve and/or needle may be used to identify the needle type.

For example, in the event of a tip type mismatch (i.e., a sleeve and/or needle not recognized by the system), the system may take appropriate steps to prevent a safety hazard.

Systems and methods for detecting the actual tip or tip type being used on the handpiece are described in U.S. Patent Application Publication 2023/0255821, which is assigned to the assignee of the current application and is incorporated herein by reference. Application 2023/0255821 describes determining the tip type during priming using a calibration chamber fitted on the tip.

However, it is often desirable to use the same vendor for the sleeve and the ophthalmic surgery system, which is not addressed in the method described in 2023/0255821. This method also does not detect an error that may occur during the very last preparation stages, such as the priming sequence, such as a tip replacement that may be done just before a physician who operates the system applies the handpiece to the eye of a patient, the eye typically being viewed under a microscope.

In some examples of the present disclosure that are described hereinafter a processor (i) receives the tip type determined by the method of application 2023/0255821, (ii) verifies the tip type using image processing, and (iii) mitigates some cases where the tip does not match the one provided by the vendor of the ophthalmic surgery system. In other examples, the processor receives the expected tip type from a stored definition of multiple tip types and multiple respective visual properties of the tip types. The expected correlation of parameters captured during the priming sequence for the different tip types is also stored.

In the disclosed technique the processor analyzes an image taken by the system's microscope to identify a tip's actual visual property, such as the color and/or shape (or, as another example, an imprinted barcode), to confirm that the correct tip was identified during priming. For example, since every sleeve has a dedicated color and, possibly, sleeve shape, such image processing can verify that the correct sleeve was identified, as follows:

(i) Sleeves of the same vendor but with different functional parameters have different colors. If the disclosed technique finds a color mismatch the system alerts the user. For example, sleeves have certain predefined colors/shades of color for each manufacturer/vendor— each color corresponds to diameter and flow rate. The processor checks the color/shade of color, and if it is, for example, not the same color/shade of color to the vendor's color/shade of color, the processor denies its use or requires a user provide additional information about the sleeve.

(ii) Sleeves manufactured by companies other than the system vendor use their own color coding and/or shape. If the disclosed technique finds a color/color shade and/or shape mismatch the system alerts the user.

In general, in case of detecting a mismatch between the actual visual property and the specified visual property of the tip, the processor takes a responsive action, that can be invoking an audiovisual alert. At this stage, the user may run the priming again or manually check the tip.

By verifying that the actual tip type conforms with requirements (i) or (ii), the disclosed technique ensures that the system settings being used correspond to the tip attached to the handpiece and that the surgical system can operate safely.

Finally, the disclosed technique offers not just verification of the sleeve and/or needle but also autodetection of such sleeve and/or needle and making sure that the sleeve and/or needle is indeed a known sleeve and/or needle for the system (given vendor's sleeves come with specific color coding and very unique colors, so a sleeve which is not original to the vendor will probably have a slightly different color).

System Description

FIG. 1 is a schematic illustration of an ophthalmic surgical system 100, in accordance with an example of the present disclosure. System 100 is an exemplary phacoemulsification/diathermy/vitrectomy system. As illustrated, system 100 includes, for example, a handpiece or wand 20 of an ophthalmic instrument 12, a replaceable tip 24 at a distal end 23 of handpiece 20, an irrigation source 30, an aspiration source 40, an optional pressure supply 50, and a control module 60. Tip 24 includes a needle 26 which extends through the lumen of a sleeve 28 to a point beyond sleeve 28. A camera 55 of the ophthalmic surgery system acquires an image of the tip, typically taken (and analyzed) while the physician prepares to perform the actual procedure and the tip being in the microscope view so an image can be taken.

A controlled fluid flow is directed through system 100 in order to irrigate a patient's eye, via tip 24, during an ocular surgical procedure. For example, irrigation source 30 may be a bag or bottle; aspiration source 40 may be, for example, a peristaltic pump, a venturi pump, a progressive cavity pump (PCP), a combination of the aforementioned pumps, and/or similar pump types known in the art; optional pressure supply 50 may be any source known in the art to supply pressure to irrigation source 30 or alternatively, a pump may be used for fluid flow from the irrigation source to an eye via handpiece 20, e.g. various types of pumps, such as, but not limited to, peristaltic, venturi, progressive cavity pump (PCP), pneumatic, or a combination thereof. At tip 24, irrigation is provided to the eye through sleeve 28 that at least partially surrounds needle 26, while aspiration is through the lumen of needle 26.

As illustrated in FIG. 1, irrigation source 30 is configured to supply a predetermined amount of fluid to handpiece 20 for use during a surgical operation. Specifically, fluid may flow from irrigation source 30 to handpiece 20 via an irrigation line 32. Irrigation source 30 may be any type of irrigation source that can create and control a constant fluid flow, such that vacuum pressure may be determined in the fluid flow, as known in the art. In illustrative examples, irrigation source 30 may be configured to be an elevated drip bag that supplies a steady state of fluid to the irrigation line 32. Pressure supply 50 may be coupled with irrigation source 30 in order to maintain a constant pressure in irrigation source 30 as fluid exits irrigation source 30, as is known in the industry. Other examples administering irrigation fluid to an eye is also envisioned, for example using a pump to move fluid from the irrigation source 30 to the eye via the handpiece, e.g., a peristaltic pump, a venturi pump, PCP, etc. known in the art.

During the surgical procedure, it is necessary to remove or aspirate fluid and other material from the eye. Accordingly, fluid may be aspirated from the eye via handpiece 20 to flow through an aspiration line 42 via an aspiration source 40. Aspiration source 40 may be any type of aspiration source that creates a constant fluid flow such that vacuum pressure may be determined in the fluid flow. In illustrative examples, aspiration source 40 may be configured to be a flow-based pump 44 (such as a peristaltic pump, scroll pump, or PCP pump). Aspiration source 40 may create an aspiration system to pump a uniform or predetermined amount of fluid and/or material out of the eye via aspiration line 42.

Handpiece 20 includes a first (proximal) end 22 and a second (distal) end 23 that includes means for attaching tip 24, which is interchangeable, depending on the specifics of the procedure. Sleeve 28 includes one or more irrigation ports and needle 26 includes an aspiration port at the distal end. Sleeve 28 is fluidly coupled with irrigation line 32 to receive fluid flow from irrigation source 30, and needle 26 is fluidly coupled with aspiration line 42 to receive fluid and/or material flow from the eye.

Handpiece 20 and tip 24 may, for example, further emit ultrasonic energy into the patient's eye via needle 26, for instance, to emulsify or break apart the crystalline lens within the patient's eye. Such emulsification may be accomplished by any known method in the industry, such as, for example, a vibrating unit (not shown) that is configured to ultrasonically vibrate and/or cut the lens, as is known in the art. Other forms of emulsification, such as a laser, are well known in the art. Concomitantly with emulsification, fluid from irrigation source 30 is irrigated into the eye via irrigation line 32 and sleeve 28. During and after such emulsification, the irrigation fluid and emulsified crystalline lens material are aspirated from the eye by aspiration source 40 via needle 26 and aspiration line 42.

Interchangeable tip 24 may be a predetermined or uniform shape and size, and typically further include various features that are beneficial to performing the surgical operation, such as various needle gauges (e.g., 19 gauge, 20 gauge and 21 gauge), the size of the sleeve, the gap between the inner wall of sleeve 28 and the outer wall of needle 26, a bend in the tip and the degree of the bend, tip flare (the inner and outer diameter increase from the shaft to the end of tip 24), and combinations thereof. Such tips 24 are generally known to be of uniform sizes or types in the industry, such that certain tips 24 may be considered advantageous for certain surgical maneuvers or operations. Tips of uniform size or type may be identified as an industry standard design by a specific name or product number. Surgeons or other users of such tips may have industry knowledge of the tip types available and their varying characteristics, and may rely on the uniformity of tip types from operation to operation. It is extremely important to correctly identify the tip being used by its type, to ensure that handpiece 20 and tip 24, comprised within system 100, function properly.

A sensor system 52 determines input (irrigation) pressure of fluid flowing through sleeve 28 (sensor 54), and output (aspiration) pressure flowing through needle 26 (sensor 56).

Sensor system 52 may be configured in a variety of ways or located in different locations. For example, sensor system 52 may include at least a first sensor or strain gauge 54 to measure irrigation pressure, and a second sensor or strain gauge 56 to measure aspiration pressure. Before fluid begins to flow through irrigation sleeve 28, the first sensor 54, such as a vacuum sensor or pressure transducer, is utilized to detect variables such as fluid pressure, or vacuum level, of fluid flowing into the eye. After the fluid and materials flow through aspiration needle 26, a second sensor 56, which may also be a vacuum sensor or pressure transducer, may be utilized to detect similar variables of the fluid flowing out of the eye via needle 26 of handpiece 20. Additional sensors 54 and 56 can also be located elsewhere along irrigation line 32 and aspiration line 42, respectively. In some examples, one or more sensors may be located on aspiration line 42, irrigation line 32, tip 24 (sleeve 28 and/or needle 26), handpiece 20, and/or a separate module coupled with the aspiration/irrigation lines 42/32 and/or handpiece 20.

System 100, for example, includes a control module 60 configured to monitor and control various components of the system. For instance, control module 60 may monitor, control, and provide power to aspiration source 40, irrigation source 30, optional pressure supply 50, and/or handpiece 20. Control module 60 may take a variety of forms as known in the art. In an illustrative example, control module 60 may include a microprocessor computer 62 having a memory 63, a keyboard 64 (which may be virtually displayed on a screen), and a display or screen 66. The microprocessor computer 62 may be connected in order to control various other elements of the system, while keyboard 64, display 66, and a foot pedal (not shown) may permit a user to interact with and control system components as well.

Microprocessor computer 62, for example, comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

For example, control module 60 may also include a pulsed ultrasonic power source (not shown) that can be controlled by computer 62 in accordance with methods or algorithms known in the art. A system bus (not shown) may be further provided to enable the various elements to be operable in communication with each other.

Screen 66 may display various measurements, criteria or settings of system 100, such as procedure type, phase of the procedure and duration of the phase, flow rate, input and output pressures, and the specific tip 24 for which the system has been calibrated. Screen 66 may be in the form of a graphical user interface (GUI) (not shown) associated with control module 60, for tip selection and settings for particular tips, and, for example, utilizing a touchscreen interface. The GUI may allow a user to monitor the characteristics of system 100 and/or select settings or criteria for various components of the system. For instance, the GUI may permit a user to select or alter the maximum pressure being supplied by pressure supply 50 to irrigation source 30. The user may further control the operation of the phase of the procedure, the units of measurement used by system 100, and the height of irrigation source 30, if applicable.

In one example, the pressure reading may be indicative of the total pressure of irrigation line 32, and may combine measurements of both the irrigation source height and the pressure provided into pressure supply line 58. In this way, for example, the GUI may provide both an actual pressure reading based on direct measurement of irrigation line 32, and a target or desired pressure based on the height of irrigation source 30 and the pressure provided in pressure supply line 58, if any. As another example, in this way rather than having pressurized infusion to the bottle, the system uses one or more PCP pumps to control both irrigation and aspiration fluid flow. The GUI may provide then actual pressure reading due to PCP pump action based on direct measurement of irrigation line 32.

The GUI may further allow for the calibration and priming of the system, as well as tuning the handpiece. The GUI may also provide other options for the user, such as, for example, allowing for canceling priming and tuning by selecting a button (or text box on a screen or touch screen).

Phacoemulsification Tip Types

FIGS. 2A and 2B are schematic diagrams of different possible sleeve colors (2A) and needle shapes (2B), of tips of the handpiece of the disclosed system in accordance with examples of the present disclosure. FIG. 2A shows sleeves from the same vendor that are color-coded by functionality (e.g., maximal attenable irrigation), such as sleeve 28 of tip 24 in FIG. 1.

FIG. 2B shows two examples of tips with different needle shapes (straight beveled and curved flare) that may be provided by the same or different vendors. Various other tip shapes, angles, and sizes are well-known in the art. Tips from different vendors may perform in a similar manner for part of an operational range, but may not match a given vendor's system design (e.g., conform to the same to pressure thresholds). Therefore, using a tip from one vendor with a system from another may result in suboptimal performance.

The present disclosure aims to ensure that the actual tip type in use is correct from a functionality and/or vendor-matching aspects.

Verification of Phacoemulsification Tip Type Using Image

Processing FIG. 3 is a flow chart of a method for verifying tip type using image processing, in accordance with an example of the present disclosure. The algorithm, according to the presented example, carries out a process that begins with determining tip type step 302, where the tip type is determined during priming using, for example, a calibration chamber, as described in the above-mentioned U.S. Patent Application Publication 2023/0255821.

Next, at tip image acquisition step 304, a camera of the ophthalmic surgery system acquires an image of the tip, typically taken (and analyzed) while the physician prepares to perform the actual procedure and the tip being in the microscope view so an image can be taken. The image may be taken when the tip is outside of the eye but within the microscope view and/or when the tip is placed into the eye and within the microscope view. The tip may also be inserted into the eye and the image may be taken when the physician is ready to press the foot pedal. At this stage, before the physician presses the pedal, the aspiration line is not engaged, therefore the irrigation line is not active either (i.e., does not output any irrigation fluid).

Processor 62 detects the tip color (e.g., the sleeve of the tip), at tip color detection step 306.

At checking step 308, the processor checks if there is a mismatch between the identified color and the expected color code (e.g., based on functional parameters of the tip established in step 302). If the answer is "yes," the processor issues an alert to the user, at alerting step 316. The alert may be audible, visual (e.g., on the GUI), tactile feedback in the handpiece or foot pedal, etc.

If the answer is "no," in an optional step (seen dashed), the process continues to a needle shape detecting step 310. At this step processor 62 detects the tip shape (e.g., the needle of the tip). At an optional shape checking step 312, the processor checks if there is a mismatch between the tip shape (e.g., needle shape) and the expected shape of a tip (e.g., needle) used by the vendor of the ophthalmic surgery system. If the answer is "yes," the processor issues an alert to the user, at alerting step 316.

If the optional step 310 is skipped or the answer to step 312 is "no," the process continues to a continue process step 314. In one example, step 314 gives a "green light" (e.g., by a visual indication on display 66) or permits activation of the system to proceed with the current tip.

The flow chart of FIG. 3 is simplified in order to provide a clear example to convey concepts of the disclosure. Other steps that may trigger action by the system may be applied that are not mentioned (such as using a foot pedal).

EXAMPLES

Example 1

A method for validating selection of a tip (24) type for a tip of a handpiece (20) of an ophthalmic instrument (12), the method includes storing in a memory (63) a definition of multiple tip types and multiple respective visual properties of the tip types. An image of the tip (24) is acquired by a camera (55) during a medical procedure using the ophthalmic instrument (12). An actual visual property of the tip is identified in the acquired image. Based on the stored definition of the multiple tip types and the multiple respective visual properties, a processor (62) determines whether the actual visual property of the tip matches a specified tip type intended for the medical procedure. A responsive action is taken in case of a mismatch between the actual visual property and the specified visual property.

Example 2

The method of example 1, wherein the handpiece (20) is a phacoemulsification probe.

Example 3

The method of any of examples 1 and 2, wherein the specified tip (24) type is determined during priming of the phacoemulsification probe in a calibration chamber.

Example 4

The method of any of examples 1 through 3, wherein the visual property is color.

Example 5

The method of any of examples 1 through 3, wherein the visual property is shape.

Example 6

The method of any of examples 1 through 5, wherein the camera (55) is part of an ophthalmic surgery system (100).

Example 7

The method of claim 4, wherein acquiring the image is performed via a microscope (55) of the ophthalmic surgery system (100).

Example 8

The method of any of examples 1 through 7, wherein acquiring the image is performed before inserting the tip (24) into an eye of a patient.

Example 9

The method of any of examples 1 through 8, wherein taking the responsive action comprises invoking an audio-visual alert.

Example 10

The method of any of examples 1 through 9, wherein the definition of multiple tip (24) types comprises respective definitions of at least one of a sleeve (28) and a needle (26) of each of the tips.

Example 11

The method of any of examples 1 through 10, wherein the tip type is a needle (26), a sleeve (28), or both the needle and the sleeve (26, 28).

Example 12

A system for validating selection of a tip (24) type for a tip of a handpiece (20) of an ophthalmic instrument (12), the system comprising a memory (63), a camera (55) and a processor (62). The memory (63) is configured for storing a definition of multiple tip types and multiple respective visual properties of the tip types. The camera (55) is configured to acquire an image of the tip (24) during a medical procedure using the ophthalmic instrument (12). The processor (62) is configured to (i) identify an actual visual property of the tip (24) in the acquired image, (ii) based on the stored definition of the tip (34) types and the multiple respective visual properties, determine whether the actual visual property of the tip (24) matches a specified tip type intended for the medical procedure, and (iii) take a responsive action in case of a mismatch between the actual visual property and the specified visual property.

Although the examples disclosed herein mainly address phacoemulsification procedures, the methods and systems disclosed herein can also be used in other applications, such as in vitrectomy surgery and other ophthalmic surgical procedures.

It will thus be appreciated that the examples described above are not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for validating selection of a tip type for a tip of a handpiece of an ophthalmic instrument, the method comprising:

storing a definition of multiple tip types and multiple respective visual properties of the tip types, wherein the definition of the multiple tip types and the multiple respective visual properties comprises respective definitions of a needle and a sleeve for each of the multiple tip types, wherein for each of the multiple tip types, the respective definitions of the needle and sleeve are different;

acquiring an image of the tip by a camera during a medical procedure using the ophthalmic instrument;

identifying an actual visual property of the tip in the acquired image, wherein the actual visual property is associated with at least one of a needle or a sleeve of the tip;

based on the stored definition of the multiple tip types and the multiple respective visual properties of the tip types, determining whether the actual visual property of the tip matches a respective visual property of a specified one of the multiple tip types intended for the medical procedure; and taking a responsive action in case of a mismatch between the actual visual property and the respective visual property of the specified one of the multiple tip types.

2. The method of claim 1, wherein the handpiece is a phacoemulsification probe.

3. The method of claim 2, wherein the specified one of the multiple tip types is determined during priming of the phacoemulsification probe in a calibration chamber.

4. The method of claim 1, wherein the actual visual property is color.

5. The method of claim 1, wherein the actual visual property is shape.

6. The method of claim 1, wherein the camera is part of an ophthalmic surgery system.

7. The method of claim 6, wherein acquiring the image is performed via a microscope of the ophthalmic surgery system.

8. The method of claim 1, wherein acquiring the image is performed before inserting the tip into an eye of a patient.

9. The method of claim 1, wherein taking the responsive action comprises invoking an audiovisual alert.

10. A system for validating selection of a tip type for a tip of a handpiece of an ophthalmic instrument, the system comprising:

a memory configured for storing a definition of multiple tip types and multiple respective visual properties of the tip types, wherein the definition of the multiple tip types and the multiple respective visual properties comprises respective definitions of a needle and a sleeve for each of the multiple tip types, wherein for each of the multiple tip types, the respective definitions of the needle and sleeve are different;

a camera configured to acquire an image of the tip during a medical procedure using the ophthalmic instrument; and a processor, which is configured to:

identify an actual visual property of the tip in the acquired image, wherein the actual visual property is associated with at least one of a needle or a sleeve of the tip;

based on the stored definition of the multiple tip types and multiple respective visual properties of the tip types, determine whether the actual visual property of the tip matches a respective visual property of a specified one of the multiple tip types intended for the medical procedure; and take a responsive action in case of a mismatch between the actual visual property and the respective visual property of the specified one of the multiple tip types.

11. The system of claim 10, wherein the handpiece is a phacoemulsification probe.

12. The system of claim 11, wherein the specified one of the multiple tip types is determined during priming of the phacoemulsification probe in a calibration chamber.

13. The system of claim 10, wherein the actual visual property is color.

14. The system of claim 10, wherein the actual visual property is shape.

15. The system of claim 10, wherein the camera is part of an ophthalmic surgery system.

16. The system of claim 15, wherein the camera is configured to acquire the image via a microscope of the ophthalmic surgery system.

17. The system of claim 10, wherein the camera is configured to acquire the image before inserting the tip into an eye of a patient.

18. The system of claim 10, wherein the processor is configured to take the responsive action by invoking an audiovisual alert.

* * * * *